US012678019B2

(12) United States Patent
George

(10) Patent No.: US 12,678,019 B2
(45) Date of Patent: Jul. 14, 2026

(54) SHOE DISINFECTING DEVICE

(71) Applicant: DG Technologies LLC, Ooltewah, TN (US)

(72) Inventor: Dillon George, Ooltewah, TN (US)

(73) Assignee: DG Technologies LLC, Ooltewah, TN (US)

( * ) Notice: Subject to any disclaimer, the term of this patent is extended or adjusted under 35 U.S.C. 154(b) by 431 days.

(21) Appl. No.: 18/217,231

(22) Filed: Jun. 30, 2023

(65) Prior Publication Data

US 2025/0000328 A1 Jan. 2, 2025

(51) Int. Cl.
| *A47L 23/02* | (2006.01) |
| *A47L 23/22* | (2006.01) |
| *A61L 2/18* | (2026.01) |
| *A61L 2/24* | (2006.01) |

(52) U.S. Cl.
CPC .............. *A47L 23/02* (2013.01); *A47L 23/22* (2013.01); *A61L 2/18* (2013.01); *A61L 2/24* (2013.01); *A61L 2202/14* (2013.01); *A61L 2202/15* (2013.01); *A61L 2202/17* (2013.01)

(58) Field of Classification Search
CPC .............. A61L 2/18; A61L 23/22; A61L 23/02
See application file for complete search history.

(56) References Cited

U.S. PATENT DOCUMENTS

| 3,973,286 A | 8/1976 | Logan |
| 5,164,164 A | 11/1992 | Strickler et al. |

| 6,668,842 B1 | 12/2003 | Wilke et al. |
| 9,457,383 B1 | 10/2016 | Skerven |
| 2003/0037395 A1 | 2/2003 | Andrews |
| 2005/0160549 A1 | 7/2005 | Dean |
| 2007/0271715 A1 | 11/2007 | Scoralle |

(Continued)

FOREIGN PATENT DOCUMENTS

| CN | 106725233 A | * | 5/2017 | ............. A47L 23/22 |
| CN | 112190217 A | * | 1/2021 | ............. A47L 23/22 |

OTHER PUBLICATIONS

English Translation of Document Identification No. CN 106725233 A provided by the United States Patent and Trademark Office search tool PE2E Search: Zhou, Rong; Water Scrubbing Sole Cleaning Machine; May 31, 2017 (Year: 2017).*

(Continued)

*Primary Examiner* — Kevin Joyner
(74) *Attorney, Agent, or Firm* — Patterson Intellectual Property Law, PC

(57) ABSTRACT

A shoe disinfecting device of the present disclosure may comprise a base, an interior compartment configured to hold a liquid disinfecting solution, at least one shoe wiping assembly including a tray and at least one absorbent pad, a first sensor configured to generate output signals representing a liquid content level of the tray, and a controller. The tray may include a recess having at least one channel defined therein. The controller may include a liquid disinfecting solution control mode configured to receive the output signals from the first sensor and, based on a comparison between the measured liquid content level and a target liquid content level, to selectively pump the liquid disinfecting solution from the interior compartment of the base via at least a liquid pump and into the channel of the shoe wiping assembly.

20 Claims, 9 Drawing Sheets

(56) References Cited

U.S. PATENT DOCUMENTS

| | | |
|---|---|---|
| 2015/0096597 A1 | 4/2015 | Patel et al. |
| 2019/0133414 A1 | 5/2019 | Barnhill et al. |
| 2020/0163532 A1* | 5/2020 | George ................... A47L 23/04 |
| 2021/0030256 A1 | 2/2021 | Ori |
| 2021/0059502 A1 | 3/2021 | Rotteveel et al. |

OTHER PUBLICATIONS

English Translation of Document Identification No. CN 112190217 A provided by the United States Patent and Trademark Office search tool PE2E Search: Yu, Jun-ping; An automatic Boot Washing Machine; Jan. 8, 2021 (Year: 2021).*

International Search Report and Written Opinion for corresponding patent application No. PCT/US2024/036107, dated Oct. 16, 2024, 10 pages.

* cited by examiner

SHOE DISINFECTING DEVICE

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

FIELD OF THE DISCLOSURE

The present disclosure relates generally to the field of disinfecting devices. More particularly, the disclosure relates to a disinfecting device which is utilized to disinfect the bottom of a shoe.

BACKGROUND

The bottoms of shoes come into direct contact with all types of unclean substances commonly found on a floor, street, sidewalk, or other walking surface. Many of these substances are riddles with bacteria or unsanitary matter. As a person walks into his or her home, these unclean substances are tracked onto the floor of the home. Any person walking or crawling on the floor now comes into direct contact with these unclean substances, therefore posing a serious health risk to that person. Moreover, these unclean substances can be tracked into and throughout a healthcare facility, thus posing a health risk to patients and healthcare workers.

Shoe disinfecting devices are known in the prior art. However, conventional shoe disinfecting devices typically spray a disinfecting solution directly onto a user's shoe. Additionally, these conventional shoe disinfecting devices lack the controls to provide a consistent amount of disinfecting solution to every shoe. This results in some of the disinfecting solution being wasted. Further, the disinfecting solution often ends up in areas not intended for cleaning, such as the tops of shoes or on the bottoms portion of a user's pants.

Accordingly, a need exists for an easy to use device that provides a manner of sanitizing the shoe in an easy and effective manner.

SUMMARY OF THE DISCLOSURE

This Summary of the Disclosure is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect in accordance with the optional embodiments disclosed herein is a shoe disinfecting device comprising a base, an interior compartment, at least one shoe wiping assembly, a first sensor, and a controller. The base may have a first end configured for placement on the floor. The interior compartment may be defined within the base and configured to hold a liquid disinfecting solution. The at least one shoe wiping assembly may be positioned on the base. The at least one shoe wiping assembly may include a tray having peripheral side walls extending upwardly to define a recess. The recess may include at least one channel defined therein. The channel may be in fluid communication with the interior compartment of the base via at least a liquid pump. The at least one absorbent pad may be positioned at least partially within the recess of the tray. The first sensor may be configured to generate output signals representing a liquid content level of the tray. The controller may include a liquid disinfecting solution control mode configured to receive the output signals from the first sensor, and based on a comparison between the measured liquid content level and a target liquid content level, to selectively pump the liquid disinfecting solution from the interior compartment of the base via at least the liquid pump and into the channel of the shoe wiping assembly.

In certain optional embodiments in accordance with this aspect, the first sensor may be a capacitance sensor.

In certain optional embodiments in accordance with this aspect, the pad may include a foraminous material.

In certain optional embodiments in accordance with this aspect, the shoe disinfecting device may further comprise at least one drying pad positioned adjacent to the at least one shoe wiping assembly.

In certain optional embodiments in accordance with this aspect, the shoe disinfecting device may further comprise at least one drying pad positioned subsequent to the shoe wiping assembly in a traveling direction.

In certain optional embodiments in accordance with this aspect, the shoe disinfecting device may further comprise a reservoir located within the interior compartment and in fluid communication with at least the liquid pump. The reservoir may be configured to hold the liquid disinfecting solution therein.

In certain optional embodiments in accordance with this aspect, the shoe disinfecting device may further comprise a second sensor configured to generate output signals representing a fluid level of the reservoir.

In certain optional embodiments in accordance with this aspect, in the liquid disinfecting solution control mode, the controller may be further configured to disable the liquid pump at least in part based on the measured fluid level of the reservoir.

In certain optional embodiments in accordance with this aspect, the shoe disinfecting device may further comprise a reference sensor configured to generate output signals representing a baseline liquid content level. In the liquid disinfecting solution control mode the controller may be further configured to calibrate the first sensor based on the baseline liquid content level.

In certain optional embodiments in accordance with this aspect, the shoe disinfecting device may further comprise a status indicator. In the liquid disinfecting solution control mode the controller may be further configured to indicate a first status when the tray reaches the target liquid content level.

In certain optional embodiments in accordance with this aspect, in the liquid disinfecting solution control mode the controller may be further configured to indicate a second status when the liquid pump is actively pumping the liquid disinfecting solution.

In certain optional embodiments in accordance with this aspect, in the liquid disinfecting solution control mode the controller may be further configured to indicate a third status when the liquid pump is disabled.

In certain optional embodiments in accordance with this aspect, in the liquid disinfecting control mode the controller may be further configured to disable the liquid pump when a user stands on the pad.

Another aspect in accordance with the optional embodiments disclosed herein is a method of controlling a shoe disinfecting device. The shoe disinfecting device may include a base, an interior compartment defined within the base and configured to hold a liquid disinfecting solution, at least one shoe wiping assembly positioned on the base, the shoe wiping assembly including a tray having peripheral sidewalls extending upwardly to define a recess, the recess including at least one channel defined therein, the channel in fluid communication with the interior compartment of the base via at least a liquid pump, at least one absorbent pad positioned at least partially within the recess of the tray, a first sensor configured to generate output signals representing a liquid content level of the tray, and a controller. The method of controlling the shoe disinfecting device may comprise receiving the output signals from the first sensor, and based on a comparison between the measured liquid content level and a target liquid content level, selectively pumping the liquid disinfecting solution from the interior compartment of the base via at least the liquid pump and into the channel of the shoe wiping assembly.

In certain optional embodiments in accordance with this aspect, the shoe disinfecting device may further include a reservoir located within the interior compartment configured to hold the liquid disinfecting solution therein and in fluid communication with at least the liquid pump, and a second sensor configured to generate output signals representing a fluid level of the reservoir. The method of controlling the shoe disinfecting device may further comprise selectively disabling the liquid pump at least in part based on the measured liquid level of the reservoir.

In certain optional embodiments in accordance with this aspect, the shoe disinfecting device may further include a reference sensor configured to output signals representing a baseline liquid content level. The method of controlling the shoe disinfecting device may further comprise calibrating the first sensor based on the baseline liquid content level.

In certain optional embodiments in accordance with this aspect, the shoe disinfecting device may further include a status indicator. The method of controlling the shoe disinfecting device may further comprise indicating a first status when the tray reaches the target liquid content level.

In certain optional embodiments in accordance with this aspect, the method of controlling the shoe disinfecting device may further comprise indicating a second status when the liquid pump is actively pumping the liquid disinfecting solution.

In certain optional embodiments in accordance with this aspect, the method of controlling the shoe disinfecting device may further include indicating a third status when the liquid pump is disabled.

In certain optional embodiments in accordance with this aspect, the method of controlling the shoe disinfecting device may further comprise disabling the liquid pump when a user stands on the pad.

Numerous objects, features and advantages of the present invention will be readily apparent to those skilled in the art upon a review of the following description in conjunction with the accompanying drawings.

DETAILED DESCRIPTION

Figures 1, 2:
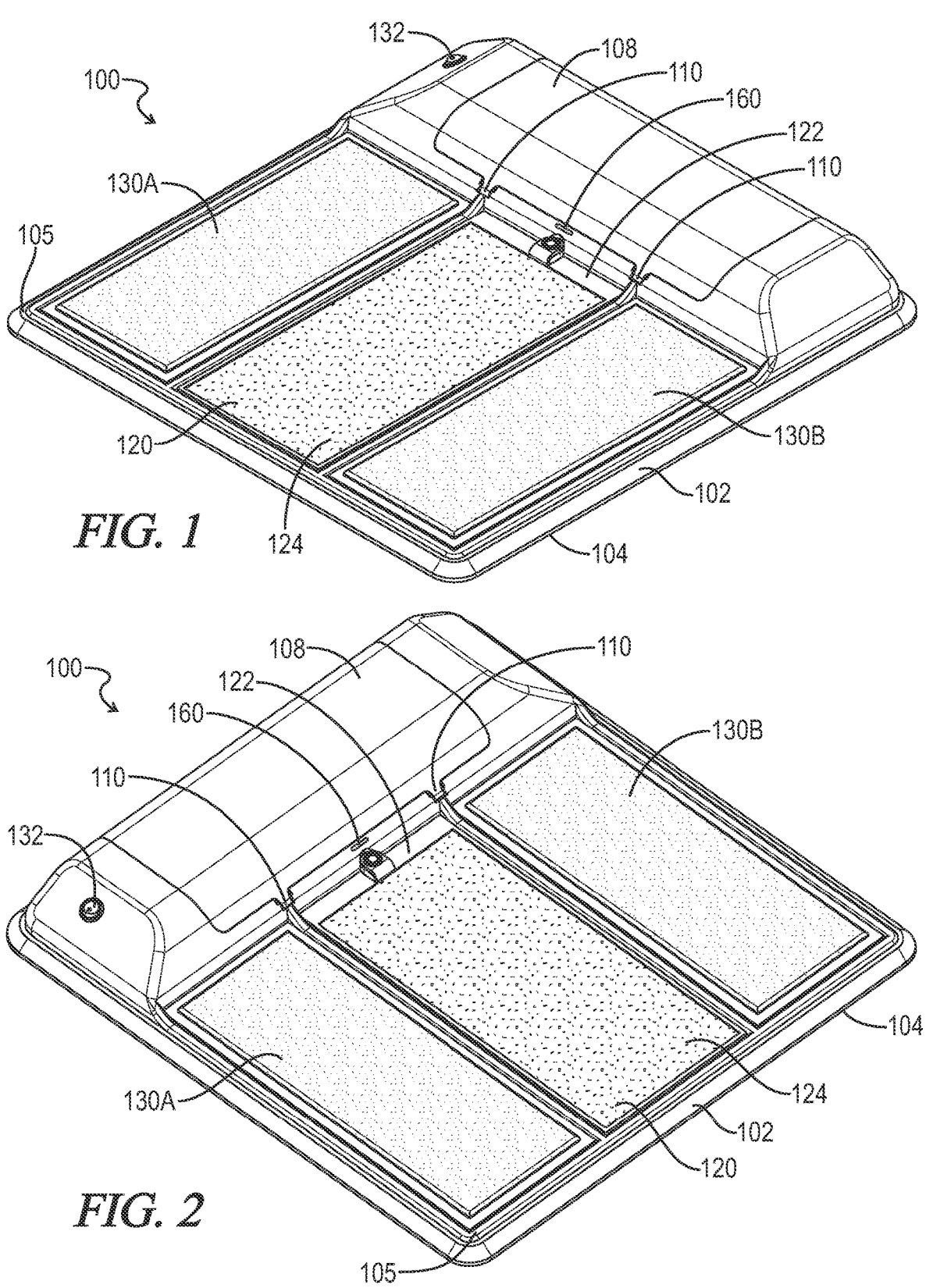
FIG. 1 is a left front perspective view of a shoe disinfecting device of the present disclosure.
FIG. 2 is a right front perspective view of the shoe disinfecting device of FIG. 1 in accordance with the present disclosure.

Reference will now be made in detail to embodiments of the present disclosure, one or more drawings of which are set forth herein. Each drawing is provided by way of explanation of the present disclosure and is not a limitation. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

Thus, it is intended that the present disclosure covers such modifications and variations as come within the scope of the appended claims and their equivalents. Other objects, features, and aspects of the present disclosure are disclosed in, or are obvious from, the following detailed description. It is to be understood by one of ordinary skill in the art that the present discussion is a description of exemplary embodiments only and is not intended as limiting the broader aspects of the present disclosure.

For purposes of the present disclosure, it is noted that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The words "connected," "attached," "joined," "mounted," "fastened," and the like should be interpreted to mean any manner of joining two objects including, but not limited to, the use of any fasteners such as screws, nuts and bolts, bolts, pin and clevis, and the like allowing for a stationary, translatable, or pivotable relationship; welding of any kind such as traditional MIG welding, TIG welding, friction welding, brazing, soldering, ultrasonic welding, torch welding, inductive welding, and the like; using any resin, glue, epoxy, and the like; being integrally formed as a single part together; any mechanical fit such as a friction fit, interference fit, slidable fit, rotatable fit, pivotable fit, and the like; any combination thereof; and the like.

Unless specifically stated otherwise, any part of the apparatus of the present disclosure may be made of any appropriate or suitable material including, but not limited to, metal, alloy, polymer, polymer mixture, wood, composite, or any combination thereof. Furthermore, any part of the apparatus of the present disclosure may be made using any applicable manufacturing method, such as, but not limited to 3D printing, injection molding, or the like.

Figure 3:
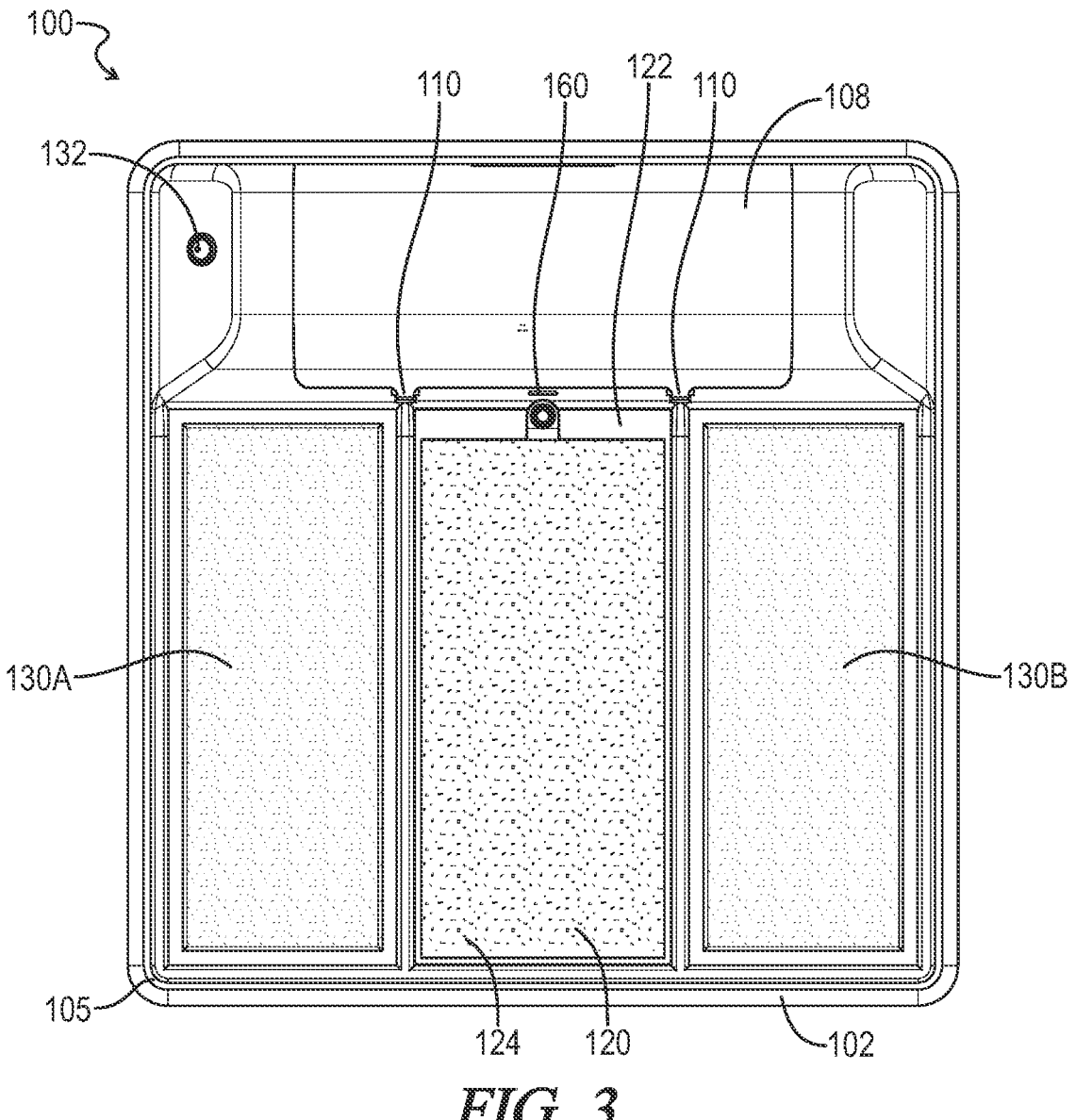
FIG. 3 is a top view of the shoe disinfecting device of FIG. 1 in accordance with the present disclosure.
Figures 4, 5:
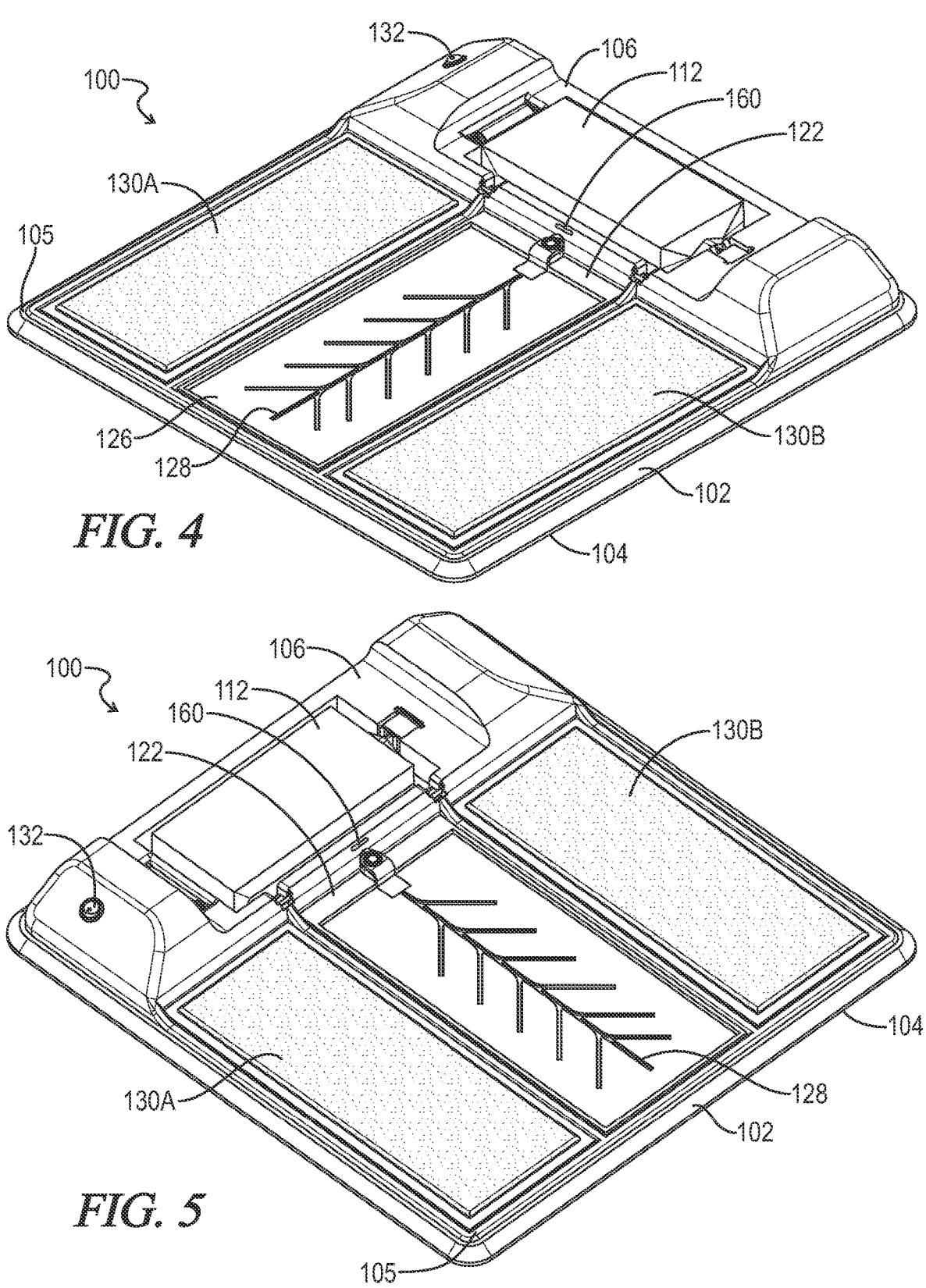
FIG. 4 is a left front perspective view of the shoe disinfecting device of FIG. 1 in accordance with the present disclosure with a lid removed.
FIG. 5 is a right front perspective view of the shoe disinfecting device of FIG. 1 in accordance with the present disclosure with the lid removed.
Figure 6:
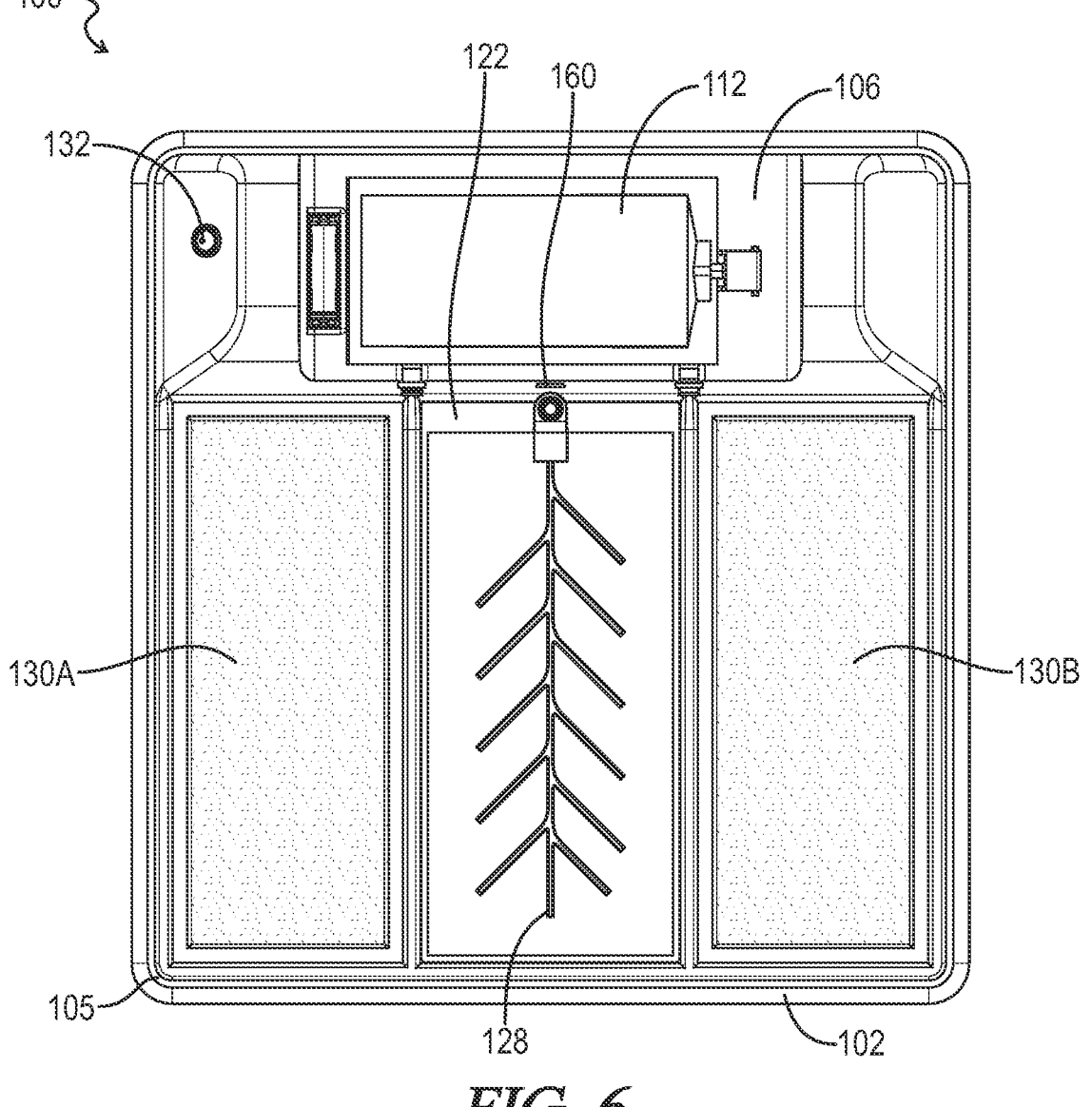
FIG. 6 is a top view of the shoe disinfecting device of FIG. 1 in accordance with the present disclosure with the lid removed.

Referring now to the figures, and specifically FIGS. 1-3, one exemplary embodiment of a shoe disinfecting device is shown and generally designated by the number 100. The shoe disinfecting device 100 may include a base 102. The base 102 of the illustrated embodiments are generally rectangular in shape, but the base 102 in other optional embodiments may be a different shape. The base 102 may have a first end 104 that is substantially flat and configured for placement on the floor. An interior compartment 106 may be defined within the base 102 opposite of the first end 104. The interior compartment 106 may be configured to receive a variety of components. The shoe disinfecting device may further include a lid 108 that may be pivotally coupled to and removable from the base 102 at pivotal connections 110 and operable to selectively cover the interior compartment 106. Thus, the lid 106 may be pivoted relative to the base 102 to expose the interior compartment 106 or to cover the interior compartment 106.

Figure 7:
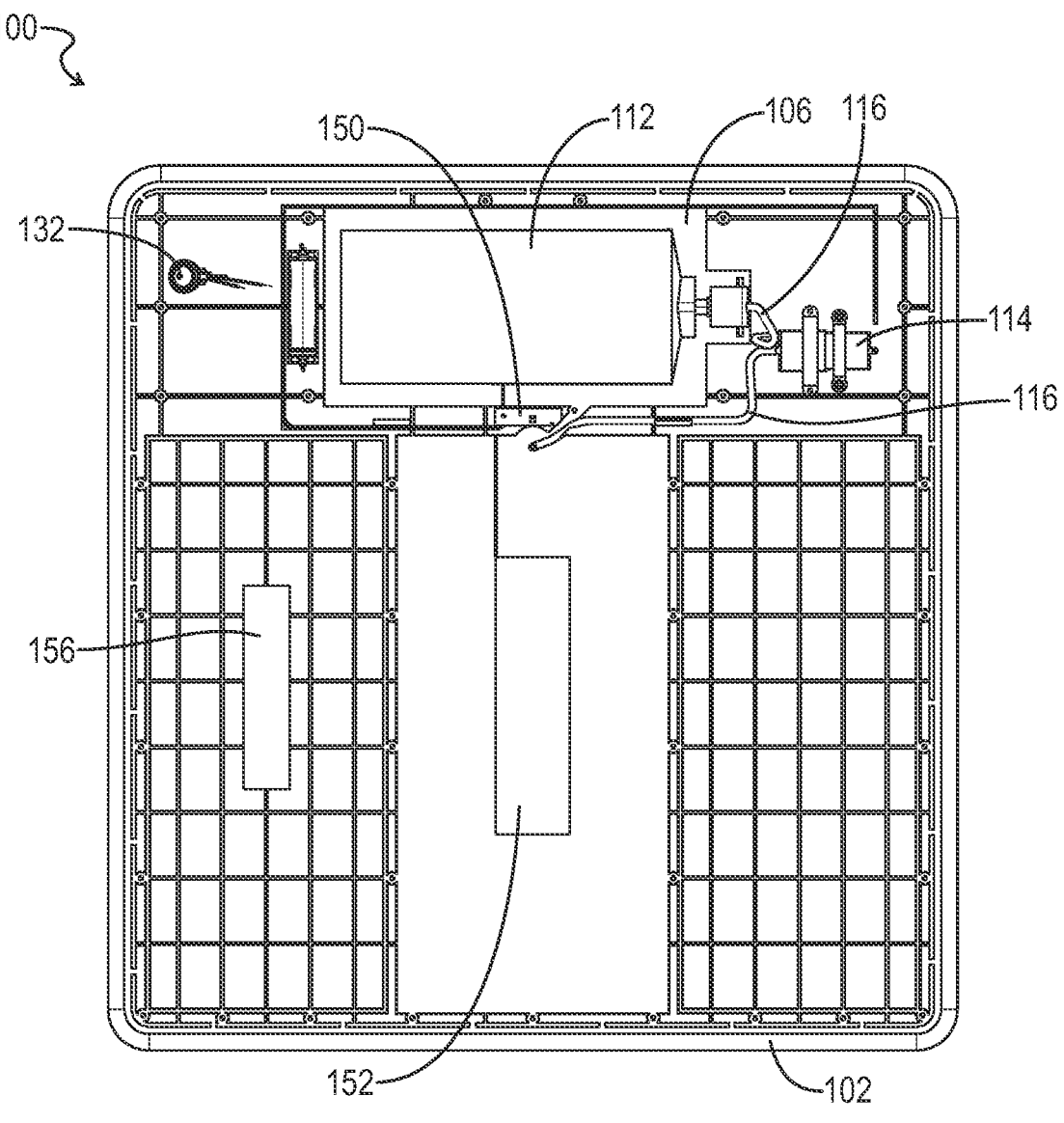
FIG. 7 is a top view of the shoe disinfecting device of FIG. 1 in accordance with the present disclosure wherein the shoe disinfecting device is partially deconstructed.
Figure 8:
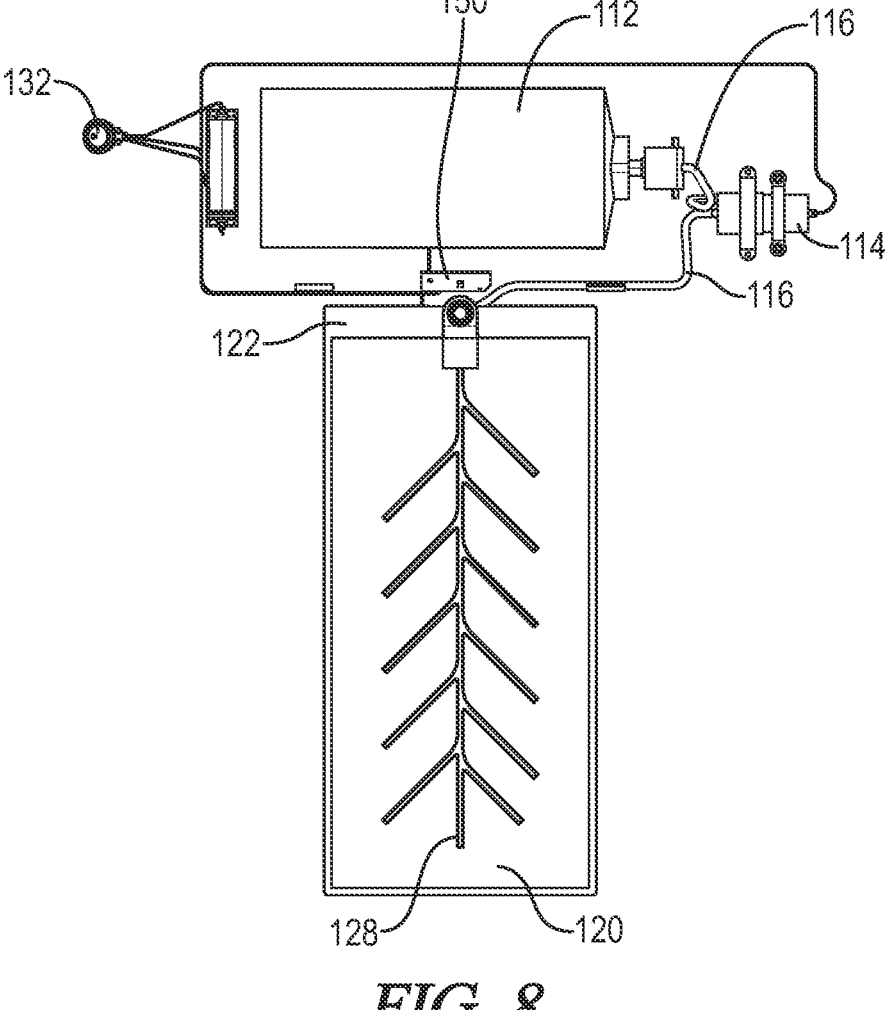
FIG. 8 is a top view of the shoe disinfecting device of FIG. 1 in accordance with the present disclosure wherein the shoe disinfecting device is partially deconstructed.
Figure 9:
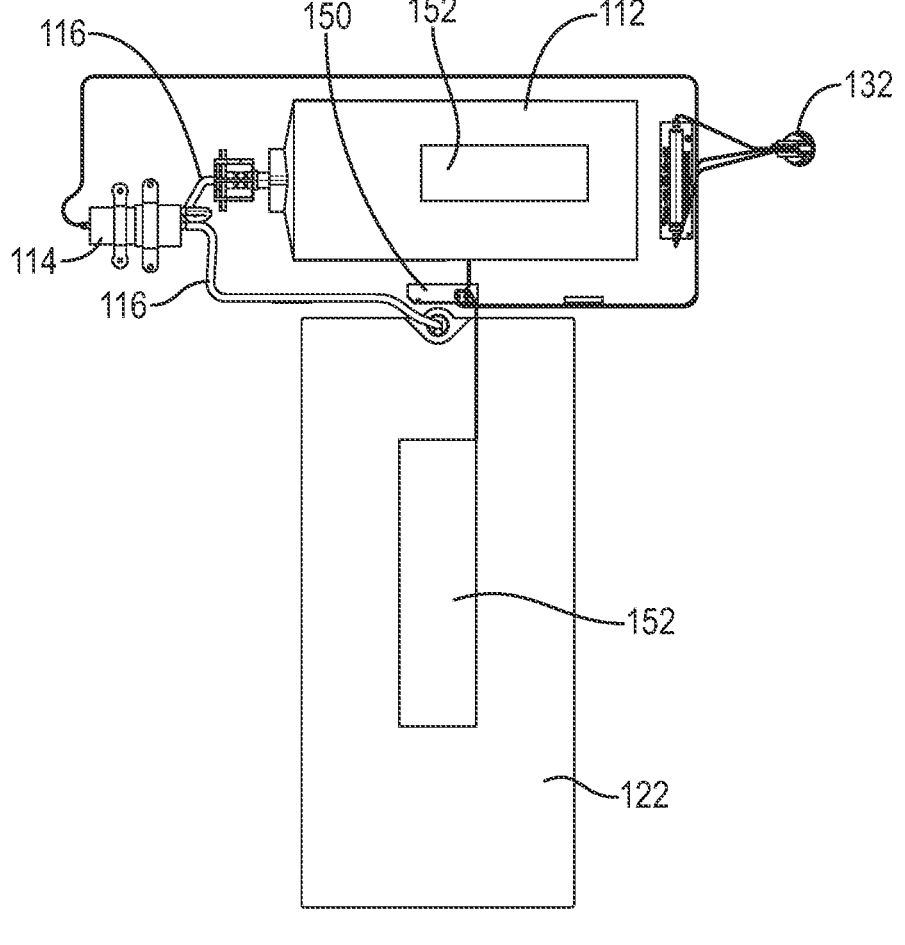
FIG. 9 is a bottom view of the shoe disinfecting device of FIG. 1 in accordance with the present disclosure wherein the shoe disinfecting device is partially deconstructed.

Referring now to FIGS. 4-9, a reservoir 112 may be located within the interior compartment 106 and configured to hold a liquid disinfecting solution therein. The reservoir 112 may be removably coupled to the base 102. The reservoir 112 may be operable to hold an amount of liquid in a range of from 200 milliliters to 800 milliliters, preferably from 300 milliliters to 700 milliliters, and most preferably from 400 milliliters to 600 milliliters. As illustrated in FIG. 7, a liquid pump 114 may also be located within the interior compartment 106 and in fluid connection with the reservoir 112. The liquid pump 114 may be fluidly connected to the reservoir 112 via a liquid feed tube 116. The liquid pump 114 may be a mechanical micropump such as a syringe pump, a peristaltic pump, self-priming diaphragm pump, a piston pump, or the like.

Figure 10:
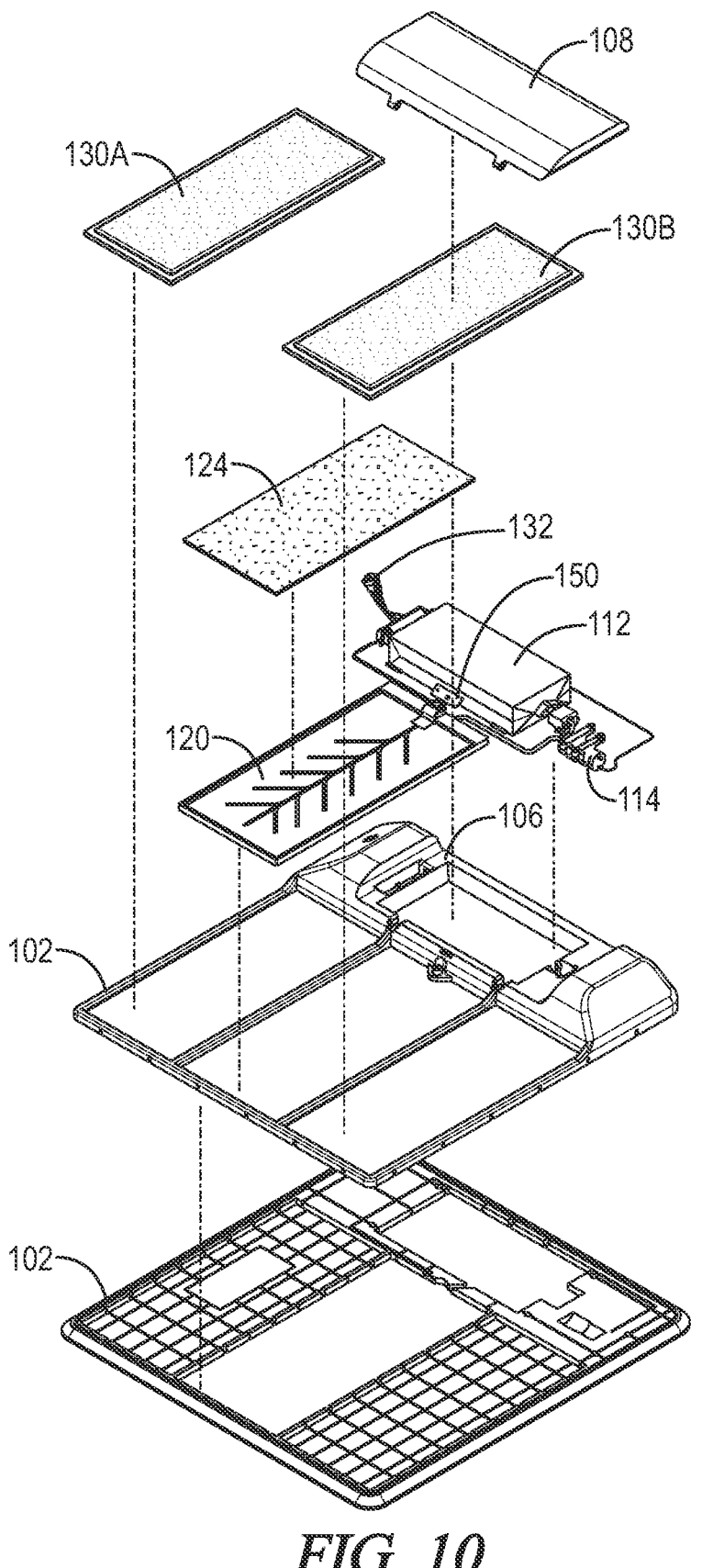
FIG. 10 is a left front exploded perspective view of the shoe disinfecting device of FIG. 1 in accordance with the present disclosure.

Best illustrated in FIG. 10, the shoe disinfecting device 100 may further include at least one shoe wiping assembly 120. While the illustrated embodiments of the shoe disinfecting device 100 includes one shoe wiping assembly 120, optional embodiments of the shoe disinfecting device 100 may include two or more shoe wiping assemblies 120. The shoe wiping assembly 120 may be positioned on a second end 105 of the base 102, opposite the first end 104. The shoe wiping assembly 120 may include a tray 122 and an absorbent pad 124.

The tray 122 may be removably coupled to the base 102. The tray 122 may have peripheral side walls extending upwardly to define a recess 126. The recess 126 may include at least one channel 128 defined therein. The at least one channel 128 may have a central portion with several secondary portions extending out from the central portion, as shown in one of the illustrated embodiment, or may be configured in alternative patterns. The at least one channel 128 may be in fluid communication with the interior compartment 106 of the base 102 via at least the liquid pump 114. More specifically, the channel 128 may be in fluid communication with the liquid pump 114 via the liquid feed tube 116, and the liquid pump 114 may be in fluid communication with the reservoir 112 via the liquid feed tube 116. Thus, the liquid disinfecting solution may be transferred from the reservoir 112, through the liquid pump 114, and into the channel 128.

The absorbent pad 124 may be positioned at least partially within the recess 126 of the tray 122. The absorbent pad 124 may be operable to be selectively removed from the recess 126. For example, the absorbent pad 124 may be removed if a user wishes to clean the absorbent pad 124 or replace the absorbent pad 124. The absorbent pad 124 may include a foraminous material, such as an open-cell foam, that can absorb or hold the liquid disinfecting solution. Alternatively, the absorbent pad 124 may be made of any material which is suitable for absorbing or holding the liquid disinfecting solution. The absorbent pad 124 may be operable to absorb the liquid disinfecting solution from the channel 128, hold the liquid disinfecting solution, and expel the liquid disinfecting solution when compressed.

The shoe disinfecting device 100 may further include at least one drying pad 130 positioned adjacent to the shoe wiping assembly 120. The at least one drying pad 130 may be received within a drying pad tray. The drying pad tray may be fixed or removably coupled to the base 102. In one illustrated embodiment, such as the illustrated embodiment of FIG. 1, the shoe disinfecting device 100 includes a first drying pad 130A and a second drying pad 130B. Each of the first and second drying pads 130A, 130B may be positioned on opposite sides of the shoe wiping assembly 120. However, the at least one drying pad 130 may be positioned on any side of the shoe wiping assembly 120.

Figures 11, 12:
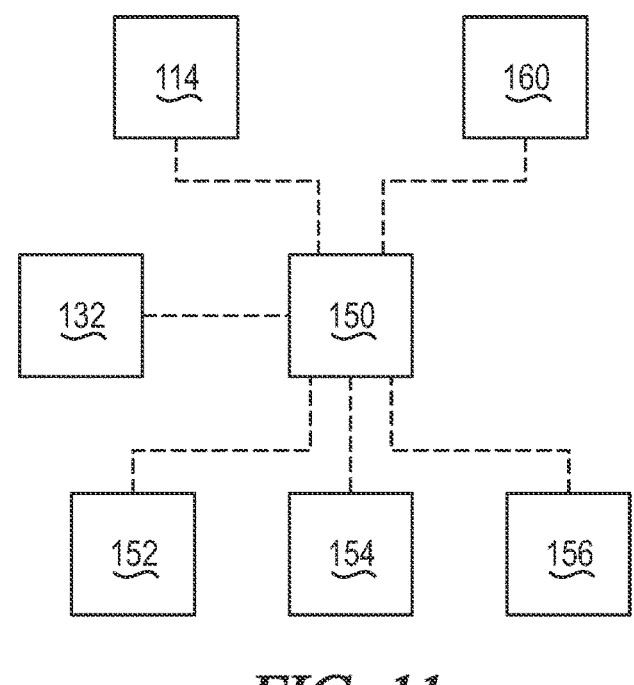
FIG. 11 is a block diagram representing an exemplary control system for the shoe disinfecting device of FIG. 1 in accordance with the present disclosure.
FIG. 12 is a front left perspective view of an optional embodiment of a shoe disinfecting device in accordance with the present disclosure.

In another illustrated embodiment, such as the illustrated embodiment of FIG. 12, the shoe disinfecting device 100 includes one and only one drying pad 130. The drying pad 130 may be located subsequent to the shoe wiping assembly 120 in a traveling direction 134. Thus, a user may move in the traveling direction 134, first stepping onto the absorbent pad 124 and subsequently stepping on the drying pad 130.

The drying pad 130 may be operable to remove the liquid disinfecting solution off of a user's shoe. The drying pad 130 may include a woven cloth or any other material that is operable to remove the liquid disinfection solution from a user's shoe. Each drying pad 130 may be selectively removed from the shoe disinfecting device 100. For example, the drying pad 130 may be removed if a user wishes to clean the drying pad 130 or replace the drying pad 130.

The shoe disinfecting device 100 may include a switch 132 configured to power the shoe disinfecting device 100 on and off. The switch 132 may be attached to the base 102 and be a two-position toggle switch.

Referring now to FIG. 11, the shoe disinfecting device 100 may include a controller 150, such as a programmable logic controller (PLC). The controller 150 may be part of a shoe disinfecting device control system or it may be a separate module. The controller 150 may be configured to receive input signals from various sensors. Similarly, the controller 150 may generate control signals for controlling the operation of the shoe disinfecting device 100.

The controller 150 includes or may be associated with a processor, a computer readable medium, a data base, and an input/output module or control panel having a display. An input/output device, such as a keyboard, joystick, or other user interface, may be provided so that the human operator may input instructions to the controller 150. It is understood that the controller 150 described herein may be a single controller having all of the described functionality, or it may include multiple controllers wherein the described functionality is distributed among the multiple controllers.

Various operations, steps, or algorithms as described in connection with the controller 150 can be embodied directly in hardware, in a computer program product such as a software module executed by the processor, or in a combination of the two. The computer program product can reside in RAM memory, flash memory, ROM memory, EPROM memory, EEPROM memory, registers, hard disk, a removable disk, or any other form of computer-readable medium known in the art. An exemplary computer-readable medium can be coupled to the processor such that the processor can read information from, and write information to, the memory/storage medium. In the alternative, the medium can be integral to the processor. The processor and the medium can reside in an application specific integrated circuit (ASIC). The ASIC can reside in a user terminal. In the alternative, the processor and the medium can reside as discrete components in a user terminal.

The term "processor" as used herein may refer to at least general-purpose or specific-purpose processing devices and/or logic as may be understood by one of skill in the art, including but not limited to a microprocessor, a microcontroller, a state machine, and the like. A processor can also be implemented as a combination of computing devices, e.g., a combination of a DSP and a microprocessor, a plurality of microprocessors, one or more microprocessors in conjunction with a DSP core, or any other such configuration.

A communications unit may support or provide communications between the controller 150 and external systems or devices, and/or support or provide communication interface with respect to internal components of the shoe disinfecting device 100. The communications unit may include wireless communications system components (e.g., via cellular modem, WiFi, Bluetooth, or the like) and/or may include one or more wired communications terminals such as universal serial bus ports.

The shoe disinfecting device may further include a first sensor 152, a second sensor 154, and a reference sensor 156. Each of the first, second, and reference sensors 152, 154, 156 may be a capacitance sensor, or alternatively may be another type of sensor such as an inductive sensor, that is in communication with the controller 150. Each of the first, second, and reference sensors 152, 154, 156 may include a thin sheet of metal foil that is attached to the base 102 substantially below the area of interest. The liquid disinfecting solution may be a mixture of water and quaternary ammonium solute that has a consistent capacitance allowing for accurate measurement by the first, second, and reference sensors 152, 154, 156. Each of the first, second, and reference sensors 152, 154, 156 may additionally function as a proximity sensor. Thus, the first sensor 152 positioned beneath the tray 122 may be configured to detect the presence of a user's shoe on the absorbent pad 124.

The first sensor 152 may be configured to generate output signals representing a liquid content level of the tray 122 to at least the controller 150. In other optional embodiments, the first sensor 152 may be configured to generate output signals representing a liquid content level of specifically the channel 128 or the absorbent pad 124. The first sensor 152 may be attached to the base 102 such that it is positioned beneath the tray 122 of the shoe wiping assembly 120. Specifically, the first sensor 152 may be positioned beneath a central portion of the tray 122 of the shoe wiping assembly 120. The first sensor 152 may additionally be configured to generate output signals representing the presence or absence of a user's shoe on the absorbent pad 124 and the presence or absence of the tray 122 on the base 102.

The second sensor 154 may be configured to generate output signals representing a fluid level of the reservoir 112 to at least the controller 150. The second sensor 154 may be attached to the base 102 such that it is positioned beneath the reservoir 112. The second sensor 154 may additionally be configured to generate output signals representing the presence or absence of the reservoir 112 from the interior compartment 106.

The reference sensor 156 may be configured to generate output signals representing a baseline liquid content level to at least the controller 150. The reference sensor 156 may be attached to the base 102 beneath an area that is not expected to contain a substantial amount of liquid disinfecting solution. For example, in the illustrated embodiment of the shoe disinfecting device 100, the reference sensor 156 is attached to the base 102 beneath the drying pad 130.

The shoe disinfecting device 100 may further include a status indicator 160. In the illustrated embodiment of the shoe disinfecting device 100, the status indicator 160 includes a light-emitting diode (LED) bulb capable of emitting light in a plurality of colors. The status indicator 160 may communicate with the controller 150 via wired or wireless connection. Each color of light emitted by the status indicator 160 may correspond to a different status of the shoe disinfecting device 100.

Liquid Disinfecting Solution Control Mode

The controller 150 includes at least a liquid disinfecting solution control mode. In the liquid disinfecting solution control mode, the controller 150 may be configured to calibrate the first and second sensors 152, 154 based on the baseline liquid content level output by the reference sensor 156. The baseline liquid content level may be a general measure of the liquid content level of the environment in which the shoe disinfecting device 100 is situated.

In the liquid disinfecting solution control mode, the controller 150 may be further configured to receive the output signals from the first sensor 152, those signals representing the liquid content level of the tray 122. Based on a comparison between the measured liquid content level and a target liquid content level, the controller 150 may be configured to selectively pump the liquid disinfecting solution from the reservoir 112 via at least the liquid pump 114 and into the channel 128 of the shoe wiping assembly 120.

The target liquid content level may be pre-programmed into the controller 150 or may be input into the controller 150 by a user. The target liquid content level represents the desired amount of liquid disinfecting solution present in the tray 122. One advantage of maintaining a target liquid content level of liquid disinfecting solution within the tray 122 may be that the absorbent pad 124 consistently maintains an amount of liquid disinfecting solution that is capable of disinfecting a bottom portion of a user's shoe. Moreover, by having the target liquid content level programmed in the controller 150, excess liquid disinfecting solution is not pumped into the tray 122, thus preventing wasting solution.

The controller 150 may be configured to pump the liquid disinfecting solution via the liquid pump 114 for a first period of time and subsequently pause for a second period of time. The first period of time may be in a range of from 0.5 seconds to 2 seconds and the second period of time may be in a range of from 2 seconds to 6 seconds, but preferably from 3 seconds to 5 seconds. During the second period of time, the controller 150 may be configured to compare the measured liquid content level and the target liquid content level. Additionally, the liquid pump 114 pausing during the second period of time may allow for the liquid disinfecting solution to soak into the absorbent pad 124 from the channel 128.

If the measured liquid content level is less than the target liquid content level, the controller 150 may be configured to repeat the process, thus pumping the liquid disinfecting solution via the liquid pump 114 for the first period of time and subsequently pausing for the second period of time. If the measured liquid content level is equal to or greater than the target liquid content level, the controller 150 will not repeat the process. When the tray 122 reaches the target liquid content level, the shoe disinfecting device 100 may be configured in a ready configuration.

In the liquid disinfecting solution control mode, the controller 150 may be configured to disable the liquid pump 114 at least in part based on the measured fluid level of the reservoir 112. For example, the controller 150 may be configured to disable the liquid pump 114 when the fluid level of the reservoir 112 is measured below a certain value.

The controller 150 may also be configured to disable the liquid pump 114 when a user stands on the absorbent pad 124. In the embodiment of the shoe disinfecting device 100 in which the first sensor 152 is a proximity sensor, the first sensor 152 may generate the output signals representing the presence of a user's shoe on the absorbent pad 124. When the controller 150 receives these output signals from the first sensor 152, the controller 150 may disable the liquid pump 114.

The controller 150 may also be configured to disable the liquid pump 114 when the reservoir 112 is removed from the base 102 or the tray 122 is removed from the base 102. In the embodiment of the shoe disinfecting device 100 in which the first sensor 152 is a proximity sensor, the first sensor 152 may generate output signals representing the absence of the tray 122. Additionally, in an embodiment of the shoe disinfecting device 100 in which the second sensor 154 is a proximity sensor, the second sensor 154 may generate output signals representing the absence of the reservoir 112. When the controller 150 receives either of these output signals from the first or second sensor 152, 154, the controller 150 may disable the liquid pump 114.

In the liquid disinfecting solution control mode, the controller 150 may be configured to indicate a first status when the tray 122 reaches the target liquid content level, also referred to herein as the shoe disinfecting device 100 being in the ready configuration. The first status may be indicated by the status indicator 160 emitting a green-colored light.

In the liquid disinfecting solution control mode, the controller 150 may be further configured to indicate a second status when the liquid pump 114 is actively pumping the liquid disinfecting solution. Thus, while the liquid pump 114 is pumping the liquid disinfecting solution from the reservoir 112 to the channel 128, the status indicator 160 may emit a blue-colored light.

In the liquid disinfecting solution control mode, the controller 150 may be further configured to indicate a third status when the liquid pump 114 is disabled. The liquid pump may be disabled at least when a user stands on the absorbent pad 124, when the reservoir 112 is removed from the base 102, or when the tray 122 is removed from the base 102. The third status may be indicated by the status indicator 160 emitting a yellow-colored light.

In the liquid disinfecting solution control mode, the controller 150 may be further configured to indicate a fourth status. In the fourth status, the shoe disinfecting device 100 is configured in a deep sleep configuration. In the deep sleep configuration, the liquid pump 114 will not pump the liquid disinfecting solution from the reservoir 112 to the channel 128. To remove the shoe disinfecting device 100 from the deep sleep configuration, a user may step on the absorbent pad 124. The first sensor 152 may then detect the presence of the user's shoe and wake the shoe disinfecting device 100 from the deep sleep configuration. The fourth status, that being the deep sleep configuration, may be indicated by the status indicator 160 not emitting any light. In other words, the LED bulb may be turned off.

In use, the liquid disinfecting solution is stored within the reservoir 112 located within the interior compartment 106 of the base 102. The user may approach the shoe disinfecting device 100 and engage the switch 132 to turn the shoe disinfecting device 100 on. The controller 150 may then receive output signals from the first, second, and reference sensors 152, 154, 156. The first and second sensors 152, 154 may be calibrated based on the output signals of the reference sensor 156. If the first sensor 152 detects that the tray 122 is removed or the second sensor 154 detects that the reservoir 112 is removed, the status indicator 160 may indicate the third status by glowing yellow and disable the liquid pump 114.

If the first sensor 152 detects the presence of the tray 122 and the second sensor 154 detects the presence of the reservoir 112, the controller 150 will compare the measured liquid content level of the tray 122 output by the first sensor 152 to the target liquid content level. If the measured liquid content level is less than the target liquid content level, the controller 150 may pump the liquid disinfecting solution from the reservoir 112 via at least the liquid pump 114 and into the channel 128 of the shoe wiping assembly 100 for the first period of time. While the liquid pump 114 is actively pumping the liquid disinfecting solution, the status indicator 160 may indicate the second status by glowing blue. The shoe disinfecting device will stop pumping for the second period of time and compare the measured liquid content level to the target liquid content level.

If, either initially on start-up or after pumping the liquid disinfecting solution into the channel 128, the measured liquid content level is equal to or greater than the target liquid content level, the status indicator 160 may indicate the first status by glowing green. Thus, the shoe disinfecting device 100 is in the ready configuration and a user may step on the absorbent pad 124. When the user steps onto the absorbent pad 124, the liquid disinfecting solution contained in the absorbent pad 124 may transfer onto at least a bottom portion of the user's shoe. The user may then step on the drying pad 130 to remove the liquid disinfecting solution and dry the bottom of the shoe.

If the embodiment of the shoe disinfecting device 100 includes one and only one drying pad 130, the user may then step off of the drying pad 130 and repeat the disinfecting process with their other shoe. Thus, the same drying pad 130 will be used for each shoe. If the embodiment of the shoe disinfecting device 100 includes at least two drying pads 130, the user may continue to stand with one shoe on the first drying pad 130A, and repeat the disinfecting process with their other shoe, this time using the second drying pad 130B.

After the user has removed their shoe from the absorbent pad 124, the first sensor 152 may detect the absence of the shoe. The controller 150 may then compare the measured liquid content level of the tray 122 to the target liquid content level and may pump the liquid disinfecting solution into the channel 128 as needed.

After a period of time in a range of from 120 minutes to 240 minutes, preferably from 140 minutes to 220 minutes, and most preferably from 160 minutes to 200 minutes, the shoe disinfecting device 100 may enter the deep sleep configuration. The status indicator 160 may indicate the fourth status by not emitting any light.

If the shoe disinfecting device 100 is configured in the deep sleep configuration and the user wishes to use the shoe disinfecting device 100, the user may step on the absorbent pad 124. The user stepping on the absorbent pad 124 may awaken the shoe disinfecting device 100. The controller 150 may then compare the measured liquid content level of the tray 122 to the target liquid content level and may pump the liquid disinfecting solution into the channel 128 as needed. Finally, the user may engage the switch 132 to turn the shoe disinfecting device 100 off.

Thus, one advantage of the shoe disinfecting device 100 disclosed herein may be that the shoe disinfecting device 100 measures and compares the liquid content level of the tray 122 to the target liquid content level. The shoe disinfecting device 100 may then pump the liquid disinfecting solution into the channel 128. The absorbent pad 124 may then absorb the liquid disinfecting solution from the channel 128. Thus, the shoe disinfecting device 100 may maintain the target liquid content level such that a user may step on the absorbent pad 124 and receive a consistent amount of liquid disinfecting solution on their shoe.

Thus, it is seen that the apparatus and methods of the present disclosure readily achieve the ends and advantages mentioned as well as those inherent therein. While certain preferred embodiments of the disclosure have been illustrated and described for present purposes, numerous changes in the arrangement and construction of parts and steps may be made by those skilled in the art, which changes are encompassed within the scope and spirit of the present disclosure as defined by the appended claims. Each disclosed feature or embodiment may be combined with any of the other disclosed features or embodiments.

What is claimed is:

1. A shoe disinfecting device, comprising:
a base having a first end configured for placement on the floor;
an interior compartment defined within the base, the interior compartment configured to hold a liquid disinfecting solution;
at least one shoe wiping assembly positioned on the base, the shoe wiping assembly including:
a tray having peripheral side walls extending upwardly to define a recess, the recess including at least one channel defined therein, the channel in fluid communication with the interior compartment of the base via at least a liquid pump;
at least one absorbent pad positioned at least partially within the recess of the tray;
a first sensor configured to generate output signals representing a liquid content level of the tray;
a reference sensor configured to generate output signals representing a baseline liquid content level; and a controller including a liquid disinfecting solution control mode configured to:
receive the output signals from the first sensor and the reference sensor;
calibrate the first sensor based on the baseline liquid content level; and
based on a comparison between the measured liquid content level and a target liquid content level, to selectively pump the liquid disinfecting solution from the interior compartment of the base via at least the liquid pump and into the channel of the shoe wiping assembly.

2. The shoe disinfecting device of claim 1, wherein the first sensor is a capacitance sensor.

3. The shoe disinfecting device of claim 1, wherein the pad includes a foraminous material.

4. The shoe disinfecting device of claim 1, further comprising at least one drying pad positioned adjacent to the at least one shoe wiping assembly.

5. The shoe disinfecting device of claim 1, further comprising at least one drying pad positioned subsequent to the shoe wiping assembly in a traveling direction.

6. The shoe disinfecting device of claim 1, further comprising a reservoir located within the interior compartment and in fluid communication with at least the liquid pump, the reservoir configured to hold the liquid disinfecting solution therein.

7. The shoe disinfecting device of claim 6, further comprising a second sensor configured to generate output signals representing a fluid level of the reservoir.

8. The shoe disinfecting device of claim 7, wherein in the liquid disinfecting solution control mode, the controller is further configured to disable the liquid pump at least in part based on the measured fluid level of the reservoir.

9. The shoe disinfecting device of claim 1, further comprising a status indicator, and wherein in the liquid disinfecting solution control mode the controller is further configured to indicate a first status when the tray reaches the target liquid content level.

10. The shoe disinfecting device of claim 9, wherein in the liquid disinfecting solution control mode the controller is further configured to indicate a second status when the liquid pump is actively pumping the liquid disinfecting solution.

11. The shoe disinfecting device of claim 10, wherein in the liquid disinfecting solution control mode the controller is further configured to indicate a third status when the liquid pump is disabled.

12. The shoe disinfecting device of claim 1, wherein in the liquid disinfecting solution control mode the controller is further configured to disable the liquid pump when a user stands on the pad.

13. A shoe disinfecting device, comprising:
a base having a first end configured for placement on the floor;
an interior compartment defined within the base, the interior compartment configured to hold a liquid disinfecting solution;
at least one shoe wiping assembly positioned on the base, the shoe wiping assembly including:
a tray having peripheral side walls extending upwardly to define a recess, the recess including at least one channel defined therein, the channel in fluid communication with the interior compartment of the base via at least a liquid pump;
at least one absorbent pad positioned at least partially within the recess of the tray;

a first sensor configured to generate output signals representing a liquid content level of the tray;

a status indicator; and a controller including a liquid disinfecting solution control mode configured to:

receive the output signals from the first sensor;

based on a comparison between the measured liquid content level and a target liquid content level, to selectively pump the liquid disinfecting solution from the interior compartment of the base via at least the liquid pump and into the channel of the shoe wiping assembly; and to indicate a first status when the tray reaches the target liquid content level.

14. The shoe disinfecting device of claim 13, wherein the first sensor is a capacitance sensor.

15. The shoe disinfecting device of claim 13, wherein the pad includes a foraminous material.

16. The shoe disinfecting device of claim 13, further comprising at least one drying pad positioned subsequent to the shoe wiping assembly in a traveling direction.

17. The shoe disinfecting device of claim 13, further comprising:

a reservoir located within the interior compartment and in fluid communication with at least the liquid pump, the reservoir configured to hold the liquid disinfecting solution therein;

a second sensor configured to generate output signals representing a fluid level of the reservoir; and wherein in the liquid disinfecting solution control mode, the controller is further configured to disable the liquid pump at least in part based on the measured fluid level of the reservoir.

18. The shoe disinfecting device of claim 13, wherein in the liquid disinfecting solution control mode the controller is further configured to indicate a second status when the liquid pump is actively pumping the liquid disinfecting solution.

19. The shoe disinfecting device of claim 18, wherein in the liquid disinfecting solution control mode the controller is further configured to indicate a third status when the liquid pump is disabled.

20. A shoe disinfecting device, comprising:

a base having a first end configured for placement on the floor;

an interior compartment defined within the base, the interior compartment configured to hold a liquid disinfecting solution;

at least one shoe wiping assembly positioned on the base, the shoe wiping assembly including:

a tray having peripheral side walls extending upwardly to define a recess, the recess including at least one channel defined therein, the channel in fluid communication with the interior compartment of the base via at least a liquid pump;

at least one absorbent pad positioned at least partially within the recess of the tray;

a first sensor configured to generate output signals representing a liquid content level of the tray; and a controller including a liquid disinfecting solution control mode configured to:

receive the output signals from the first sensor;

based on a comparison between the measured liquid content level and a target liquid content level, to selectively pump the liquid disinfecting solution from the interior compartment of the base via at least the liquid pump and into the channel of the shoe wiping assembly; and disable the liquid pump when a user stands on the pad.

* * * * *